(12) United States Patent
Wang

(10) Patent No.: US 7,097,364 B2
(45) Date of Patent: Aug. 29, 2006

(54) OPTICAL CURING APPARATUS

(76) Inventor: Shu-Lung Wang, 6F, No. 70, Sec. 1, Kuang-Fu Rd., San-Chung City,Taipei Hsien (TW)

( * ) Notice: Subject to any disclaimer, the term of this patent is extended or adjusted under 35 U.S.C. 154(b) by 204 days.

(21) Appl. No.: 10/859,177

(22) Filed: Jun. 3, 2004

(65) Prior Publication Data

US 2005/0271329 A1    Dec. 8, 2005

(51) Int. Cl.
*G02B 6/36* (2006.01)
*F21V 5/00* (2006.01)
*A61C 3/00* (2006.01)

(52) U.S. Cl. .......................... 385/76; 385/77; 385/12; 385/147; 385/901; 362/573; 433/29

(58) Field of Classification Search .................. 385/12, 385/31, 147, 901, 76, 77; 362/573; 433/29
See application file for complete search history.

(56) References Cited

U.S. PATENT DOCUMENTS 5,203,696 A * 4/1993 Gonser .................... 433/29
5,290,169 A * 3/1994 Friedman et al. .......... 433/29
5,476,379 A * 12/1995 Disel ......................... 433/29
6,179,611 B1 * 1/2001 Everett et al. .............. 433/29
6,186,944 B1 * 2/2001 Tsai ........................... 600/200
6,692,251 B1   2/2004 Logan et al. ............... 433/29
2003/0081430 A1 * 5/2003 Becker ....................... 362/573

* cited by examiner

*Primary Examiner*—Brian M. Healy
(74) *Attorney, Agent, or Firm*—Birch, Stewart, Kolasch & Birch, LLP

(57) ABSTRACT

An optical curing apparatus includes a front shell body which consists of a first shell and a second shell that are coupled in a detachable and turnable manner. A light channeling member is fastened to the first shell and may be adjusted angularly to suit user's requirements. The light channeling member and the first shell are detachable. They are adaptable to the light channeling member of various diameters, and may be removed for sterilizing, or become a disposable and replaceable item. A radiation member and an electric power supply unit are provided and detachably coupled through a connector. The radiation member is reusable even if the case is damage or other elements are breakdown.

9 Claims, 5 Drawing Sheets

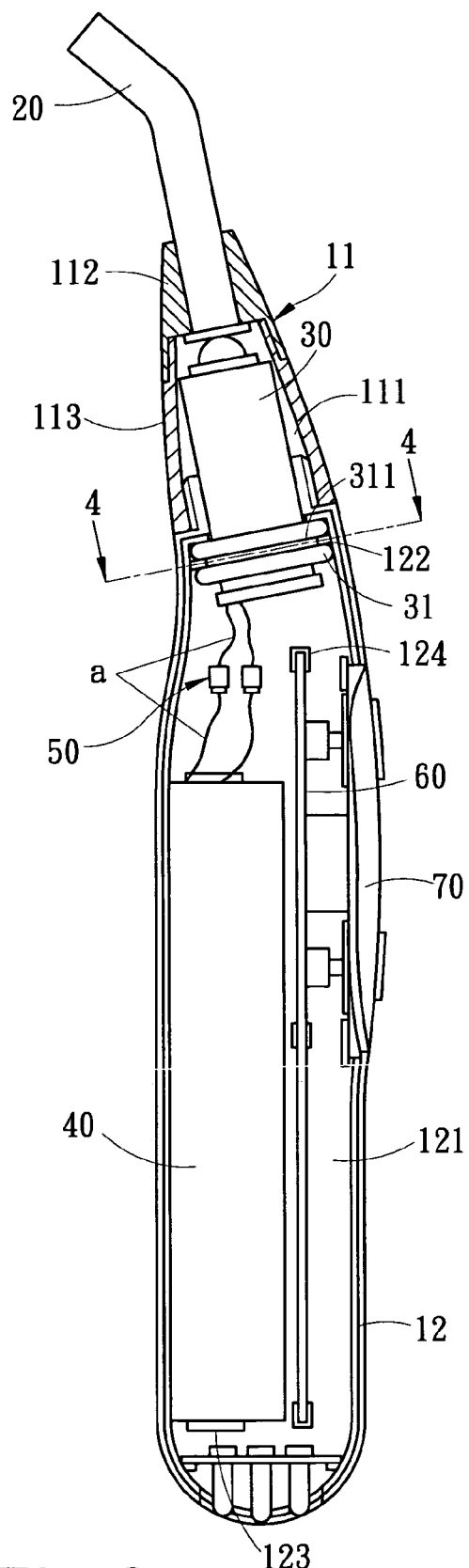
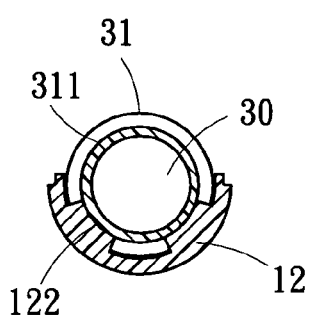
Fig.4
Fig.3

OPTICAL CURING APPARATUS

FIELD OF THE INVENTION

The present invention relates to an optical curing apparatus and particularly to an apparatus for curing dental material through optical radiation.

BACKGROUND OF THE INVENTION

Optical curing dental material is often used by dentists in the curing process, such as bonding or processing a filler in a tooth cavity and cementing the filler on a desired position. As the oral cavity has a limited space for optical curing process, the general optical curing apparatus often includes an elongate and narrow light channeling member such as a bundle of optical fibers with a free end which may be moved close to the optical curing material so that light can be directly projected to the material. U.S. Pat. No. 6,692,251B1 entitled "Apparatus and method for curing materials with light radiation" discloses an apparatus that has a light channeling member removable from the light source so that it may be sterilized for use on different patients. But in practice, not only the light channeling member has to be placed deeply into the oral cavity and might be in contact with the oral cavity, the case rim of the light channeling member also often touches patient's mouth or saliva. While the light channeling member may be detached for sterilizing, the case rim cannot be removed for this purpose. It is not hygienic and has the concern of infecting diseases. This is a serious flaw of medical practice that has to be resolved immediately.

Moreover, the cited reference has the entire structure formed like a gun. As the light channeling member is not turnable, to stick the light channeling member into the oral cavity to cement the material on the upper molar teeth, the entire gun structure has to be turned. The operation originally designed cannot be applied. It is not convenient to use. Furthermore, the light channeling members have different types such as the cylindrical one which has the same diameter for the entire length and the conical one which has varying diameters. Hence the case has to mate the outside dimension of the light channeling member. This hinders interchangeable function. In other words, different light curing apparatus have to be procured to match different types and sizes of light channeling members. This increases the cost of medical equipment and results in waste. It also makes carrying difficult, and needs a larger storage space.

In addition, the radiation member in the conventional optical curing apparatus is an important element and quite expensive. The radiation member in the conventional structure generally is directly held in the case. Heat of the radiation member directly transfers to the plastic case and could results in brittle or deformation of the case, and make the apparatus not appealing. This cannot meet the clean and hygienic requirements in the practice of dentistry. Moreover, as the radiation member is most expensive element in the whole optical curing apparatus, in the event that the case or other element is damaged, the entire apparatus has to be replaced. It is costly. In the conventional structure, the radiation member is directly bonded to the connection lines of the battery. When to replace the battery, the radiation member is difficult to remove. As the radiation member is expensive, it cannot be thrown away with the battery, hence it creates a lot of problems in maintenance. To throw the radiation member away with the battery will increase the maintenance cost. All this indicates that there is a lot of rooms for improvement in terms of economic effectiveness, cost and applicability.

SUMMARY OF THE INVENTION

The primary object of the invention is to provide an optical curing apparatus that has a front shell body which consists of a first shell and a second shell that are detachable and turnable relative to each other, and are coupled by screwing. The first shell and the second shell may be turned 360 degrees relative to each other so that the angle of the light channeling member may be adjusted as required. As the light channeling member and the first shell are detachable, they may be adapted to the light channeling members of various sizes, and may be removed for sterilizing, or become a disposable item to increase medical hygienic quality.

Another object of the invention is to make the radiation member and electric power supply unit detachable through a connector set and also make the radiation member spaced from the case at a selected interval.

Yet another object of the invention is to provide an anchor plate to hold the electric power supply unit and confine it on a desired location without escaping.

The foregoing, as well as additional objects, features and advantages of the invention will be more readily apparent from the following detailed description, which proceeds with reference to the accompanying drawings.

BRIEF DESCRIPTION OF THE DRAWINGS

FIG. 3 is a sectional view of the invention showing the entire interior structure.
FIG. 4 is a cross section taken line 4—4 in FIG. 3.

DETAILED DESCRIPTION OF THE PREFERRED EMBODIMENTS

Figure 1:
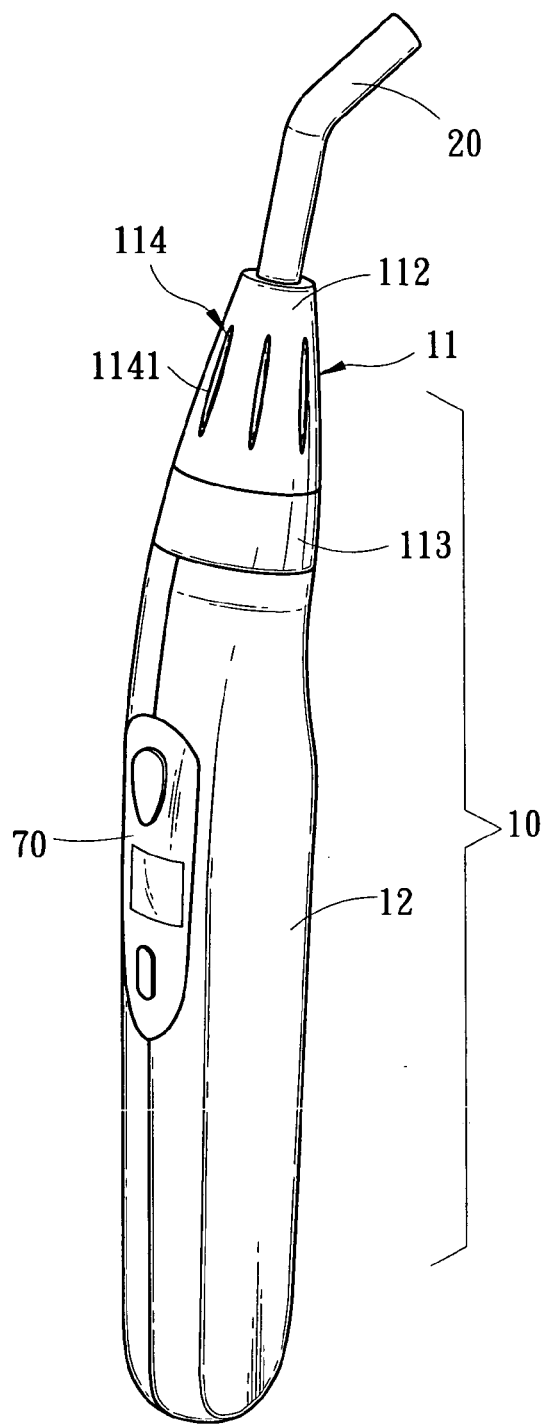
FIG. 1 is a perspective view of the invention.

The optical curing apparatus of the invention mainly aims at curing material used in dentistry. Please referring to FIGS. 1 and 3, the present invention includes:

a case 10 consisting of a front shell body 11 and a rear shell body 12. The front shell body 11 has a housing section 111 and has a front end coupling with a light channeling member 20. The rear shell body 12 is formed with an external shape for user grasping when in use, and has a housing compartment 121 to hold various elements.

Figure 2:
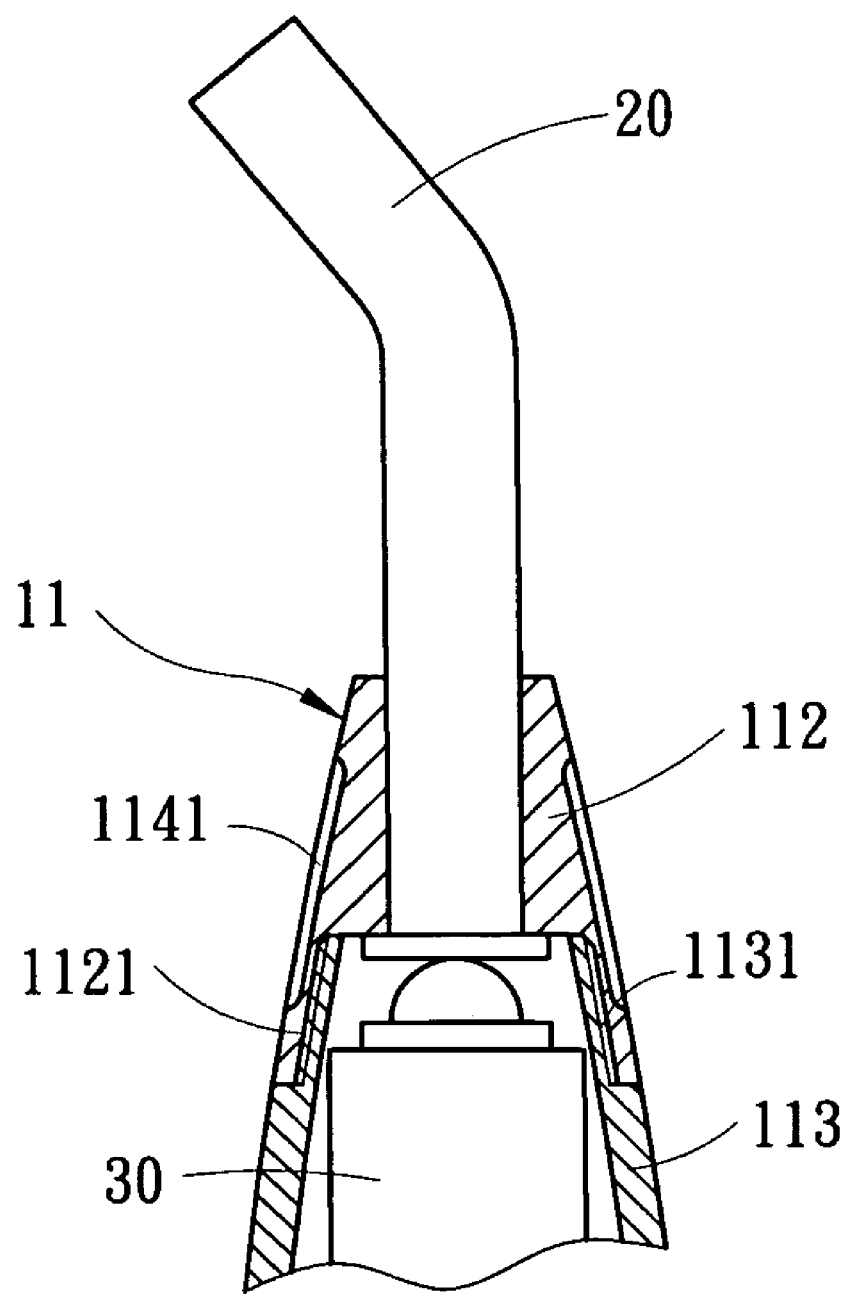
FIG. 2 is a fragmentary sectional view of the detachable front shell body of the invention.

The front shell body 11 is detachable and turnable for 360 degrees. It includes a first shell 112 and a second shell 113. The first shell 112 has internal screw threads 1121 to couple with external screw threads 1131 formed on the second shell 113. Such a screwing design allows the first shell 112 and the second shell 113 to be turnable relative to each other for 360 degrees (referring to FIG. 2). The first shell 112 further has a form an operating section 114 to facilitate turning of the first shell 112 and the second shell 113 during operation.

The rear shell body 12 has a pair of holding seats 122 close to the coupling location with the front shell body 11 to hold a radiation member 30. The radiation member 30 has an outer rim coupling with a spacer 31 which has a groove 311 formed on the surface to couple with the holding seats 122 so that the radiation member 30 is saddled on the holding seats 122 and spaced from the rear shell body 12 at a selected distance. Thereby heat from the radiation member 30 is prevented from directly transferred to the rear shell body 12 (referring to FIG. 4).

Moreover, there is a pair of anchor plates 123 located on one side of the housing compartment 121 to brace and anchor an electric power supply unit 40 in the housing compartment 121 without escaping. The electric power supply unit 40 is connected to the radiation member 30 through a wire a and a connector 50. The wire a has a portion connected to the electric power supply unit 40 that has a distal end fastened to a male connector 51, and the wire a has another portion connected to the radiation member 30 that has a distal end fastened to a female connector 52 so that the electric power supply unit 40 and the radiation member 30 may be connected in a detachable manner (referring to FIG. 5B).

The housing compartment 121 has a plurality of coupling members 124 on another side to hold a control unit 60 which is connected to an operation face panel 70 mounted on the outer surface of the rear shell body 12. Users can operate the control unit 60 through the operation face panel 70.

Figure 5A:
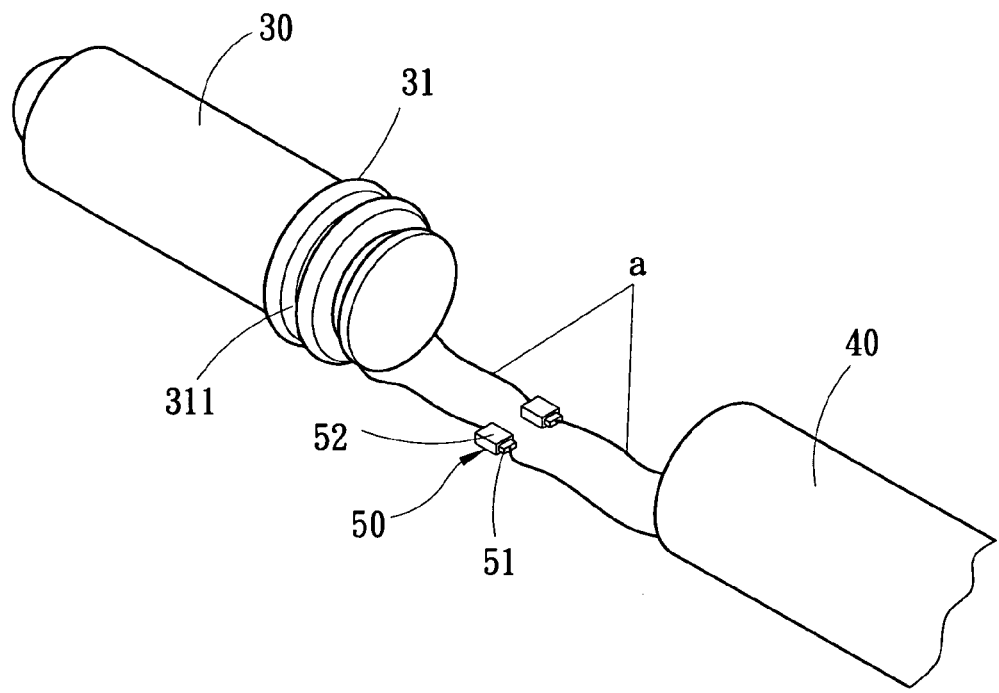
FIG. 5A is a schematic view of the radiation member and the electric power supply unit coupling through a connector.
Figure 5B:
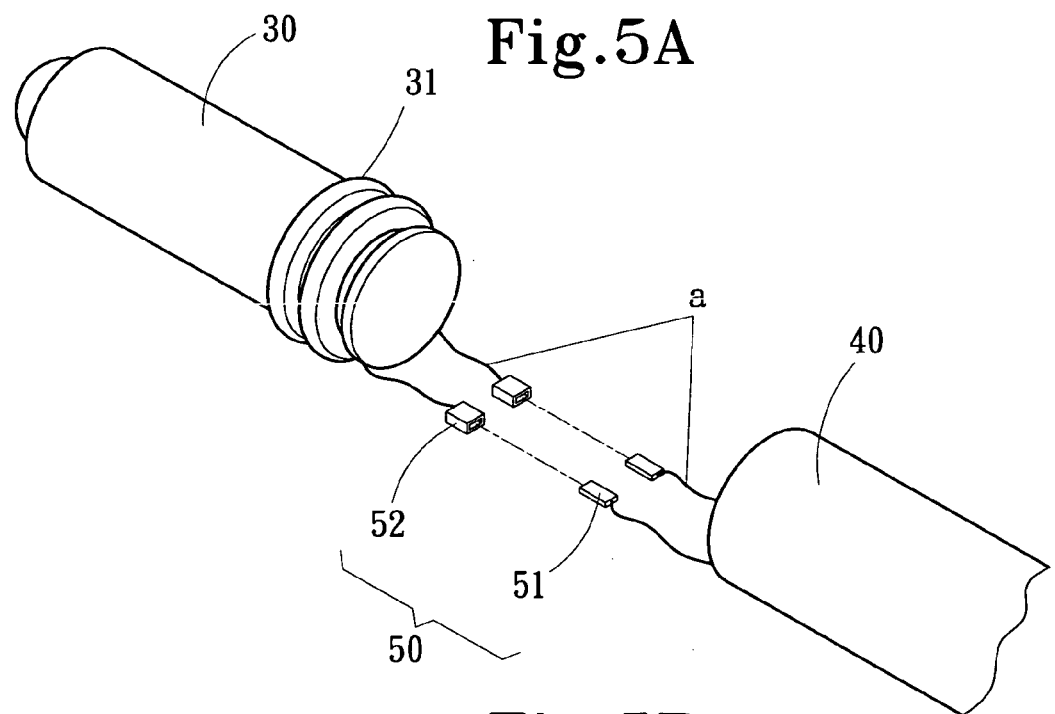
FIG. 5B is a schematic view of the radiation member and the electric power supply unit detaching through a connector.

Refer to FIGS. 5A and 5B for detaching operation of the radiation member 30. The electric power supply unit 40 and the radiation member 30 are connected through the wire a and the connector 50. The wire a connected to the electric power supply unit 40 has a distal end fastened to the male connector 51, and the wire a connected to the radiation member 30 has a distal end fastened to the female connector 52 so that the electric power supply unit 40 and the radiation member 30 may be connected in a detachable manner. Therefore the expensive radiation member 30 of the original producer may be removed to install on another optical curing apparatus of another brand or model to achieve modularization requirement. For users, as the expensive radiation member 30 adopts the detachable design, in the event that the case 10 is damage or other elements are breakdown, only the case 10 or other elements that are less costly have to be replaced, while the radiation member 30 may be used repeatedly. Hence fabrication or maintenance cost is reduced, and economic effectiveness improves.

Figure 6:
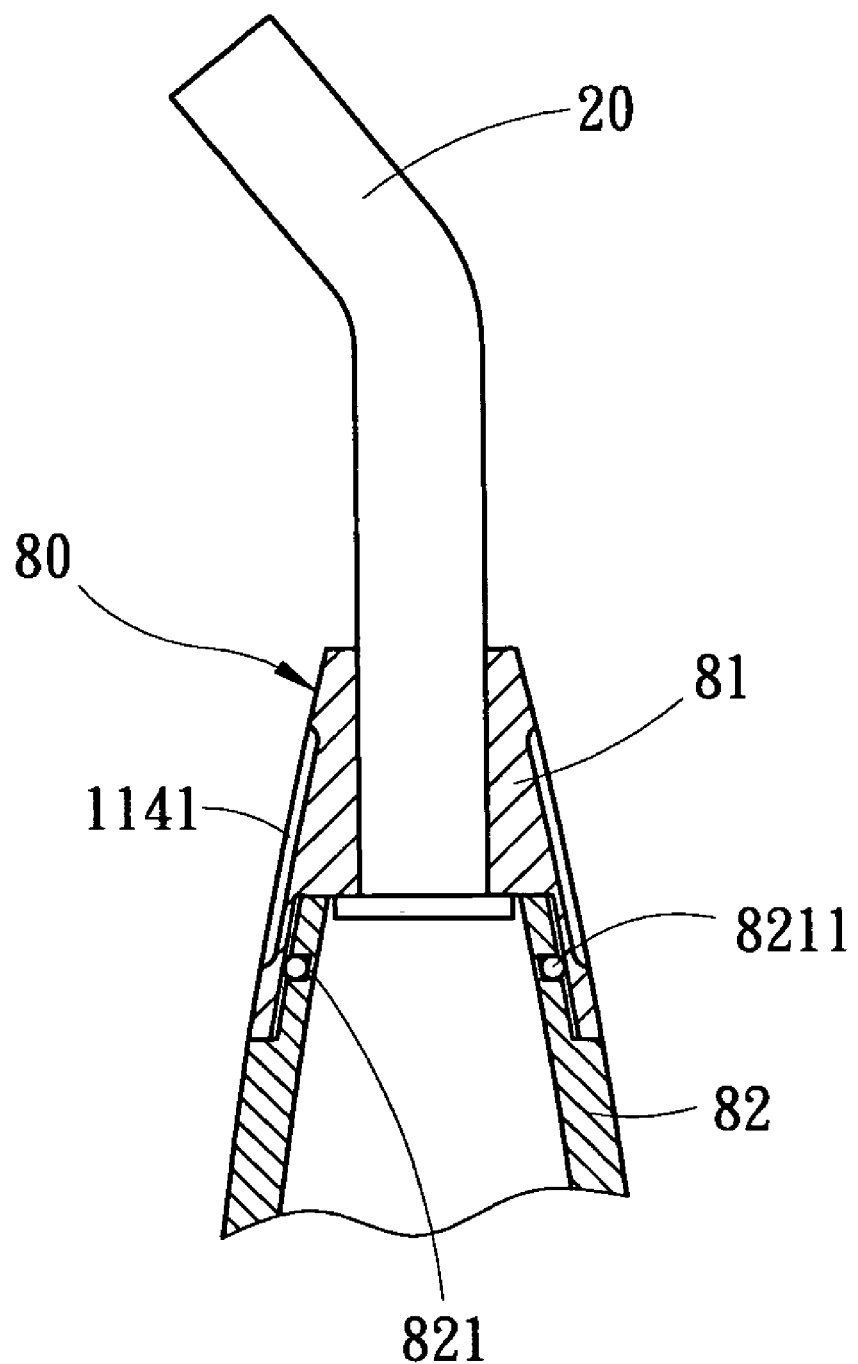
FIG. 6 is a fragmentary sectional view of another embodiment of the detachable front shell body of the invention.

Refer to FIG. 6 for another embodiment of the invention. It mainly aims to a front shell body 80 that is turnable 360 degrees. The front shell body 80 includes a first shell 81 and a second shell 82 that are coupled together. The second shell 82 on the coupling location has an annular groove 821 to hold an O-ring 8211 which provides an elastic and tight coupling with the first shell 81 without loosening off easily and also allows the first shell 81 to be detached rapidly and conveniently from the second shell 82. The elasticity of the O-ring 8211 also enables the first shell 81 and the second shell 82 to rotate 360 degrees relative to each other. Thereby user can adjust the angle as desired when in use. As the light channeling member 20 is fastened to the first shell 81 which may be detached from the second shell 82, different types and sizes of light channeling member 20 may be used. Thus it is a modular design that has a greater interchange capability. This also improves patient's oral hygiene.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. An optical curing apparatus for curing dental material, comprising:
    a control unit;
    a radiation member;
    an electric power supply unit, the electric power supply unit being coupled to the radiation member;
    a case, the case housing the control unit, the radiation member, and the electric power supply unit; and
    a light channeling member located at one end of the case abutting the radiation member;
    wherein the case includes a first shell and a second shell on the one end of the case, the first shell and the second shell being coupled together and turnable relative to each other.

2. The optical curing apparatus of claim 1, wherein the case has a holding seat corresponding to the radiation member, the radiation member being coupled with a spacer from outside for mounting on the holding seat, and being detachably coupled with the electric power supply unit through a connector.

3. The optical curing apparatus of claim 1, wherein the case has a pair of anchor plates to brace and confine the electric power supply unit in the case.

4. The optical curing apparatus of claim 1, wherein the case includes a front shell body and a rear shell body that are coupled by screwing, the light channeling member being fastened to one end of the front shell body.

5. The optical curing apparatus of claim 4, wherein the front shell body includes the first shell and the second shell that are coupled by screwing and turnable relative to each other in a helical fashion.

6. The optical curing apparatus of claim 4, wherein the front shell body includes the first shell and the second shell that are interposed by an O-ring such that the first shell and the second shell are coupled tightly in a detachable manner and turnable with each other.

7. The optical curing apparatus of claim 1, wherein the connector includes a male connector on one end of the electric power supply unit and a female connector on one end of the radiation member to allow the electric power supply unit and the radiation member to be coupled in a detachable manner.

8. The optical curing apparatus of claim 1, wherein the light channeling member is received by the first shell, the radiation member is disposed in the second shell, and the first shell and the second shell are coupled together and turnable relative to each other.

9. The optical curing apparatus of claim 1, wherein the first shell and the second shell are co-axial.

* * * * *